United States Patent
Edison (10) Patent No.: US 10,956,612 B2
(45) Date of Patent: Mar. 23, 2021

(54) HIGHLY SECURE NETWORKED SYSTEM AND METHODS FOR STORAGE, PROCESSING, AND TRANSMISSION OF SENSITIVE PERSONAL INFORMATION

(71) Applicant: Optum, Inc., Minnetonka, MN (US)

(72) Inventor: Robin Edison, Highland Park, IL (US)

(73) Assignee: Optum, Inc., Minnetonka, MN (US)

(*) Notice: Subject to any disclaimer, the term of this patent is extended or adjusted under 35 U.S.C. 154(b) by 221 days.

(21) Appl. No.: 15/517,772

(22) PCT Filed: Oct. 7, 2015

(86) PCT No.: PCT/US2015/054444
§ 371 (c)(1),
(2) Date: Apr. 7, 2017

(87) PCT Pub. No.: WO2016/108983
PCT Pub. Date: Jul. 7, 2016

(65) Prior Publication Data
US 2017/0249481 A1    Aug. 31, 2017

Related U.S. Application Data

(60) Provisional application No. 62/060,898, filed on Oct. 7, 2014.

(51) Int. Cl.
G06F 21/62     (2013.01)
G16H 10/60     (2018.01)
(Continued)

(52) U.S. Cl.
CPC ...... *G06F 21/6263* (2013.01); *G06F 21/6245* (2013.01); *G16H 10/60* (2018.01);
(Continued)

(58) Field of Classification Search
CPC .............. G06F 21/6254; G06F 19/321; G06F 21/6245; G06F 21/60; G06F 17/277; H04L 63/04; H04L 63/0272; G16H 10/60
See application file for complete search history.

(56) References Cited

U.S. PATENT DOCUMENTS 7,013,315 B1    3/2006  Boothby
7,870,614 B1    1/2011  Duhaime
(Continued)

OTHER PUBLICATIONS

International Search Report of PCT/US2015/054444, dated Jul. 1, 2016.

*Primary Examiner* — Ali S Abyaneh
(74) *Attorney, Agent, or Firm* — Seyfarth Shaw LLP; Brian Michaelis (57) ABSTRACT

A highly secure networked system and methods for storage, processing, and transmission of sensitive information are described. Sensitive, e.g. personal/private, information is cleansed, salted, and hashed by data contributor computing environments. Cleansing, salting, and hashing by multiple data contributor computing environments occurs using the same processes to ensure out put hashed values are consistent across multiple sources. The hashed sensitive information is hashed a second time by a secure facility computing environment. The second hashing of the data involves a private salt inaccessible to third parties. The second hashed data is linked to previously hashed data (when possible) and assigned a unique ID. Data dictionaries are created for particular individuals provided access to the highly secure information, e.g. researchers. Prior to a data dictionary being accessible by a researcher computing device, the data dictionary undergoes compliance and statistical analyses regarding potential re-identification of the source unhashed data. The data dictionaries are viewable by researchers as certified views via a secure VPN.

19 Claims, 9 Drawing Sheets

(51) Int. Cl.
*H04L 9/06* (2006.01)
*H04L 29/06* (2006.01)
*G06F 19/00* (2018.01)

(52) U.S. Cl.
CPC ........ *H04L 9/0643* (2013.01); *H04L 63/0272* (2013.01); *H04L 63/083* (2013.01); *G06F 19/328* (2013.01); *H04L 2463/082* (2013.01)

(56) References Cited

U.S. PATENT DOCUMENTS

| | | | |
|---|---|---|---|
| 9,984,245 B2* | 5/2018 | Schmitt | G06F 21/53 |
| 2002/0073138 A1 | 6/2002 | Gilbert et al. | |
| 2005/0268094 A1 | 12/2005 | Kohan et al. | |
| 2006/0123461 A1* | 6/2006 | Lunt | G06F 21/6254 |
| | | | 726/1 |
| 2007/0145123 A1* | 6/2007 | Yoshioka | G06Q 20/02 |
| | | | 235/380 |
| 2008/0072290 A1* | 3/2008 | Metzer | G06F 17/30348 |
| | | | 726/3 |
| 2008/0147554 A1* | 6/2008 | Stevens | G06F 21/6254 |
| | | | 705/51 |
| 2009/0300770 A1 | 12/2009 | Rowney et al. | |
| 2012/0110469 A1 | 5/2012 | Magarshak | |
| 2012/0158699 A1* | 6/2012 | Creel | G06F 17/30893 |
| | | | 707/722 |
| 2012/0303616 A1 | 11/2012 | Abuelsaad et al. | |

* cited by examiner

| UNIQUE_ID | FIRST_NAME_E|LAST_NAME_E|SSN_E |
|---|---|
| 94425100 | 1238ca657102ae567mc8845167957a78a1cd321342ca09d82a28am53a7e5830fd89\|123m812ae83f17a8488bbm9f5f0d2m74c46m94e2f42a6bd76d96614f71a6fd1efac\|123fcee4cf166e0f1d0c110338942f6a8cb1049e78c594ef49952aed348cdda3e63 |
| 94425101 | 123bff7m485135c547322b677792b39m0d8b08bcd8896m9m3699a3bmb6e7b6e205a\|1231dd4m4e87f2486ee1e639a38b3e5942d68a9118b107354abacb9me34a7509ee072b9234b38a2f3a1a9d537824cb\|1237546m08f4857e29c90f3ffc3e3em0641d6456 |
| 94425102 | 1232e6c27e28c72a14a20c07e138d45d7fca52333f673f560fc4678c734db8ddaf1\|123c2edcd9b53e3b6966efb2b201f52441dd677d2987bcca3d063577e882cb6m1d9\|123b5e9329e72f942c27ea570a1946de34b10463f55ef366c89556a2a5bf372e634 |

HIGHLY SECURE NETWORKED SYSTEM AND METHODS FOR STORAGE, PROCESSING, AND TRANSMISSION OF SENSITIVE PERSONAL INFORMATION

CROSS-REFERENCE TO RELATED APPLICATION DATA

This application claims priority to U.S. Provisional Patent Application Ser. No. 62/060,898, which is incorporated herein by reference in its entirety.

FIELD OF TECHNOLOGY

The present disclosure relates generally to secure networks, and more particularly to securing information within a network of computers.

BACKGROUND

Various industries collect personal information about individuals. Regardless of the particular industry, personal information is considered highly sensitive and often needs to be secured in an attempt to prevent unauthorized access. For example, in the healthcare context, healthcare providers often use locally maintained computing platforms to manage and secure patient records. These locally maintained computer platforms allow the healthcare providers to satisfy their duties under industry and government standards, such as the Health Insurance Portability and Accountability Act ("HIPAA").

Often times, researchers and other third parties desire access to personal information. In the healthcare industry, personal information cannot be released to researchers until it is secured. However, modern computer technology frequently makes it possible to reverse engineer the "secure" personal information into its unsecure source data. This is undesirable because it gives third parties unauthorized access to sensitive personal information.

SUMMARY

The present disclosure generally provides a highly secure networked system and methods for storage, processing, and transmission of sensitive, such as personal/private, information. Data contributor computing environments store sensitive personal information. The personal information is cleansed by a data contributor computing environment using specific rules/logic provided to data contributor computing environments by a secure facility computing environment. The secure facility computing environment transmits the same rules/logic to each data contributor computing environment. Thus, cleansing of data at each data contributor computing environment occurs the same way.

The cleansed personal information is salted (using a public salt) and hashed using a one-way hashing algorithm. Each data contributor computing environment uses the same public salt and one-way hashing algorithm. This ensures that cleansed personal information for a particular individual or grouping of individuals associated with any given contributor computing environment is hashed into an identically structured hashed field or record across multiple data contributor computing environments (i.e. all contributing computing environments provide data to be secured from that facility structured in the same manner).

Data (at least partially including the hashed personal information) is communicated from the data contributor computing environments to the secure facility computing environment. The hashed personal information is therein salted and hashed a second time using a private salt and a one-way hashing algorithm. The private salt is maintained solely within the secure facility computing environment, and is not communicated to or otherwise accessible to third parties (i.e., data contributor computing environments and/or third party, e.g. researcher, computing devices). This further secures the private data in a manner that prevents third parties from re-identifying the second hashed personal information into its unhashed source data.

The second hashed personal data value is linked to previously second hashed data values (when possible) and is assigned a unique ID. This linking of the data values to a unique ID provides a robust secure data platform, e.g. for research or data mining, because unhashed data of one data contributor computing environment is linked and accessible along with related data of other data contributor computing environments via the unique IDs.

In one embodiment, particular individuals provided access to the highly secure information such as researchers, desiring access to data, identify parameters for a research project. In response, the secure facility computing environment compiles data from various sources (linked using unique IDs) into a data dictionary. The data dictionary undergoes compliance and statistical analyses related to the potential of a researcher re-identifying the unhashed source data. When the data dictionary satisfies the compliance and statistical analyses, the data dictionary is stored and presented to the researcher as a certified view.

A researcher may be granted access to one or more certified views via a virtual private network. Each certified view may be presented through a different virtual desktop interface. Access to the certified views, via the virtual private network, by a researcher computer may involve a two factor authentication process. In this manner, a technical solution is provided to permit, among other things, stores of private data to be securely maintained as private data while otherwise being made available in further secure fashion to certified users in a limited and controlled manner.

BRIEF DESCRIPTION OF THE DRAWINGS

Embodiments of devices, systems, and methods are illustrated in the figures of the accompanying drawings, which are meant to be exemplary and non-limiting, in which like references are intended to refer to like or corresponding parts, and in which.

DETAILED DESCRIPTION

The detailed description of the present disclosure set forth herein makes reference to the accompanying drawings, which show various embodiments by way of illustration. While these various embodiments are described in sufficient detail to enable those skilled in the art to practice the disclosure, it should be understood that other embodiments may be realized and that logical and physical changes may be made without departing from the spirit and scope of the disclosure. Thus, the detailed description herein is presented for purposes of illustration only and not of limitation. For example, the steps recited in any of the method or process descriptions may be executed in an order other than as presented and are not limited to the order presented. Moreover, references to a singular embodiment may include plural embodiments, and references to more than one component may include a singular embodiment.

The present disclosure provides extensive and specialized processes for transforming personal information into secure data. The present disclosure additionally provides particularized databases containing vast amounts of de-identified medical claims, electronic medical records, and other data, such as sociodemographic information collected from consumer research databases structured to provide automated access to vast amounts of information. While the illustrative embodiments described herein may relate to healthcare information, it should be appreciated that secure systems as described may be implemented according to the disclosure for protection and transformation of other types of sensitive information such as financial information, legal information, national security information, or the like (generally referred to herein as "personal" or "private" information). The sophisticated, specialized, and specially configured networked systems and processes described herein, for example, may facilitate data driven healthcare research without compromising privacy with respect to sensitive personal information (again, the information protected, could just as readily be other information requiring high levels of security, privacy and control while facilitating controlled access for manipulation and processing). Specifically, the systems in the illustrated embodiment are configured to provide, among other things, high levels of security of vast amounts of personal/private data while simultaneously providing access to the secure personal/private data in a way that benefits the healthcare industry and its patients.

Protection and security of personal digital data is a persistent technical problem that arose after the advent of the computer. The problem is exacerbated by the proliferation of use of digital devices and the volumes of data collected, accessible and processed by such devices. An additional technical problem relates to maintaining security and privacy of vast amounts of personal data while providing digital access to the data for research aimed at furthering use and utility of the vast amounts of data, such as for enhancing consumer and patient outcomes and the delivery of healthcare. It will become apparent from reading the below detailed description that these technical problems are solved by the various teachings herein.

Figure 1:
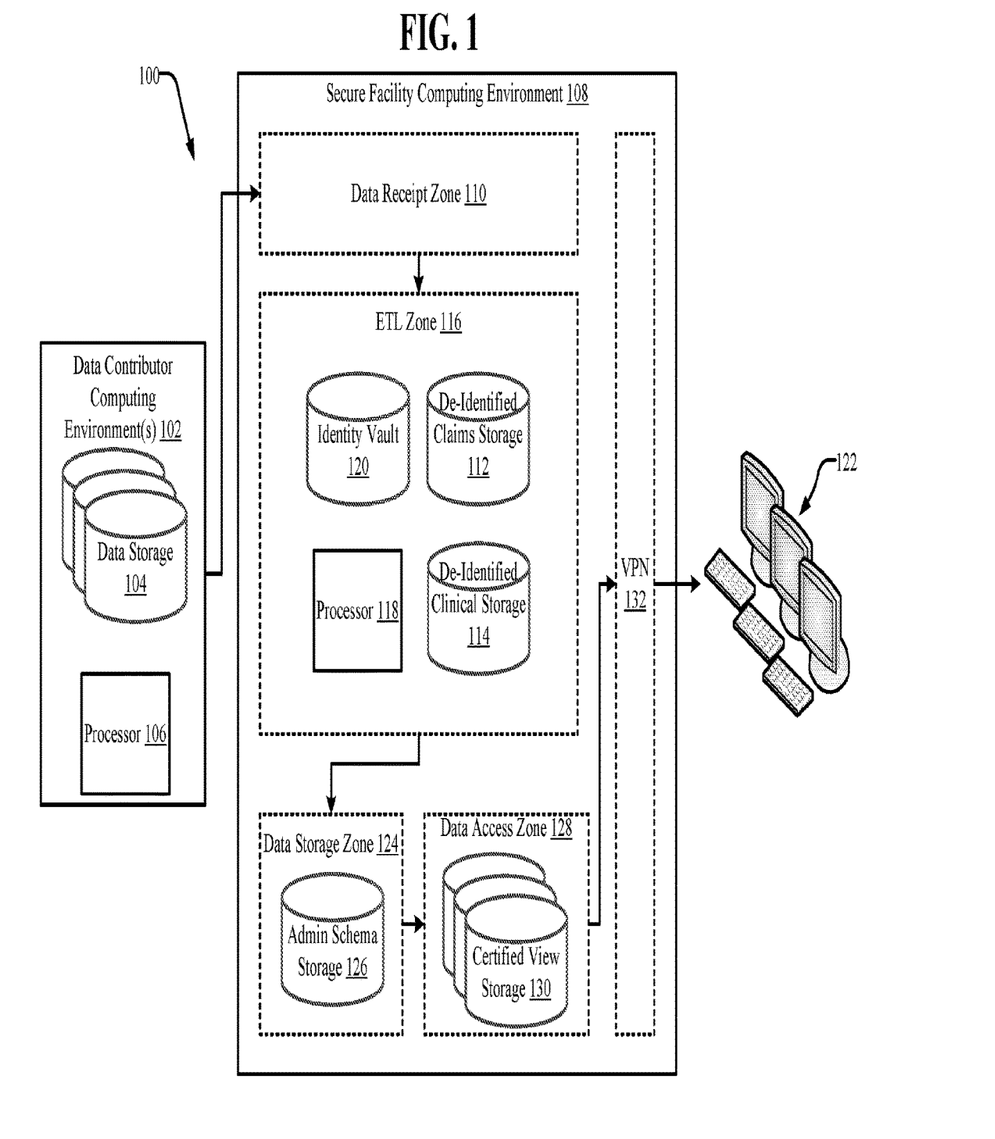
FIG. 1 illustrates an embodiment of a secure networked system for securing personal/private information and providing limited/controlled access to the secure personal information according to the present disclosure.

Referring to FIG. 1, a secure networked system 100 for securing personal information and providing limited and controlled access to the secure data is described. The system 100 includes one or more data contributor computing environments 102. Each data contributor computing environment 102 includes a data storage 104 that houses clear text data. For example, the clear text data may include healthcare claims data and clinical data that are each partially made up of personal information. The clear text healthcare claims data may be separate and distinct data from the clear text clinical data. Each data contributor computing environment 102 also includes a processor 106 that is in communication with the data storage 104 and that is configured to sanitize or cleanse and hash the personal information as described herein below with respect to FIGS. 2A and 2B.

Generally, the cleansed, hashed personal information and associated clear text non-personal information is communicated to a data receipt zone 110 of a secure facility computing environment 108. Transmission of the data may occur actively by the processor 106 (i.e., the data receipt zone 110 passively receives the data). Alternatively, transmission of the data may occur passively with respect to the data contributor computing environment 102 (i.e., a processor of the secure facility computing environment 108 may actively retrieve the data from the data contributor computing environment 102). The transmission of such data may happen in real time or it may happen in batch processes. At the data receipt zone 110, the data is staged and prepared for subsequent processing as disclosed herein below.

The cleansed data is loaded into and stored within respective storage or databases. For example, healthcare claims data and clinical data may be stored within databases, such as a de-identified claims storage 112 and a de-identified clinical storage 114 of an extract, transform, and load (ETL) zone 116 of the secure facility computing environment 108, respectively. A processor 118 of the ETL zone 114 hashes the previously hashed personal information a second time, as described herein below with reference to FIGS. 2A and 2B.

The second hashed personal information values are stored within an identity vault 112. The newly hashed and stored personal information values are thereafter "linked" by the processor 118 as described with reference to FIG. 3 below. Once a unique ID is associated with a recently stored personal information value, the same unique ID is associated with the cleansed and second hashed data (within the various storages) to which it relates. For example, when the data is healthcare data, the unique ID is associated within the cleansed, second hashed claims data and clinical data stored within the de-identified claims and clinical storages 116, 118.

Prior to the cleansed, second hashed data being stored within various storage databases, it may be processed to change encounter IDs, provider IDs, and facility IDs, provided by the data contributor computing environment(s) 102, into sequential alternate IDs. This helps eliminate trace back of the de-identified cleansed data to its source data stored within the data storage 104 of the data contributor computing environment 102.

When a researcher, via a researcher computing device 122, indicates they want to conduct research, a "data dictionary" is created from the clinical and claims data within the de-identified claims and clinical storages 112, 114. The data dictionary is essentially a description of the data presented in a certified view. The data that makes up a data dictionary may be specific to a geographic area/location, membership (e.g., membership in a particular coverage plan or program), a data domain, data type, or some other interest defined by the researcher. For example, an illustrative data dictionary may contain indicators such as table name, field name, business description, and various parameters including data type, field length, and valid values.

The generated data dictionary is communicated to a data storage zone 124 where the data dictionary is analyzed for compliance with respect to clarity/proprietary standards. The data storage zone 124 includes an admin schema storage 126 that stores rules/logic relating to clarity/proprietary standards that data must comply with prior to being viewable by a researcher. One illustrative rule identifies fields of data that present re-identification risk and that should be removed from the data dictionary. Another illustrative rule identifies fields that present re-identification risk and contain values that should be consolidated to lessen the risk. An illustrative and non-limiting list of such data values includes bed size, discharge status, and admit channels. A further illustrative rule identifies fields that require standard language to comply with auditing. Yet another illustrative rule may identify fields that are required to be flagged as potentially identifying personal information characteristics.

Various statistical de-identification rules/logic may also be applied to the data dictionaries while in the data storage zone 124. The statistical de-identification rules/logic use statistical methodology to evaluate data of a data dictionary as well as public records to, through reduction of data and consolidation of values, achieve a statistical determination of a very small risk of re-identification. A threshold risk value of re-identification of de-identified data may be set as a function of, for example, geographic location, number of patients, age, timing of disease occurrence, number of providers, or related data. The statistical de-identification rules/logic may be stored within the admin schema storage 126 or a separate storage (not illustrated).

When a data dictionary passes the compliance standards, as set out by the rules/logic of the data storage zone 124, the data dictionary is communicated to a data access zone 128 where it is stored in a certified view storage 130. Each certified view storage 130 may include only one data dictionary. Alternatively, each certified view storage 130 may contain all of the certified views approved for viewing by a single researcher, or certified views may require no storage. A researcher can view different certified views from different desktops in the manner of one and only one view per desktop. This prevents unauthorized access to certified views by unapproved researchers. While there may be overlap (e.g. common data) between two certified views it may be desirable for security purposes that each certified view is wholly independent of another.

A researcher may indicate they desire a previously approved certified view to be augmented to include more types of data. When this occurs, the other data types are identified within the data storages 112, 114. This data is then compiled into the original data of the certified view. The updated data compilation thereafter undergoes the aforementioned compliance and statistical analyses described with respect to the generation of a new data dictionary. If the augmented certified view is analyzed to have a very small risk of source data re-identification, it is stored as an updated certified view and is published to the researcher(s) authorized to view the original certified view.

The secure facility computing environment 108 also includes a virtual private network (VPN) 132 that is configured to restrict researcher computer 122 access to certain certified views. The structure of the VPN 132 and its interaction with the data access zone 128 and researcher computers 122 is described in further detail below with respect to FIG. 7.

Figure 2A:
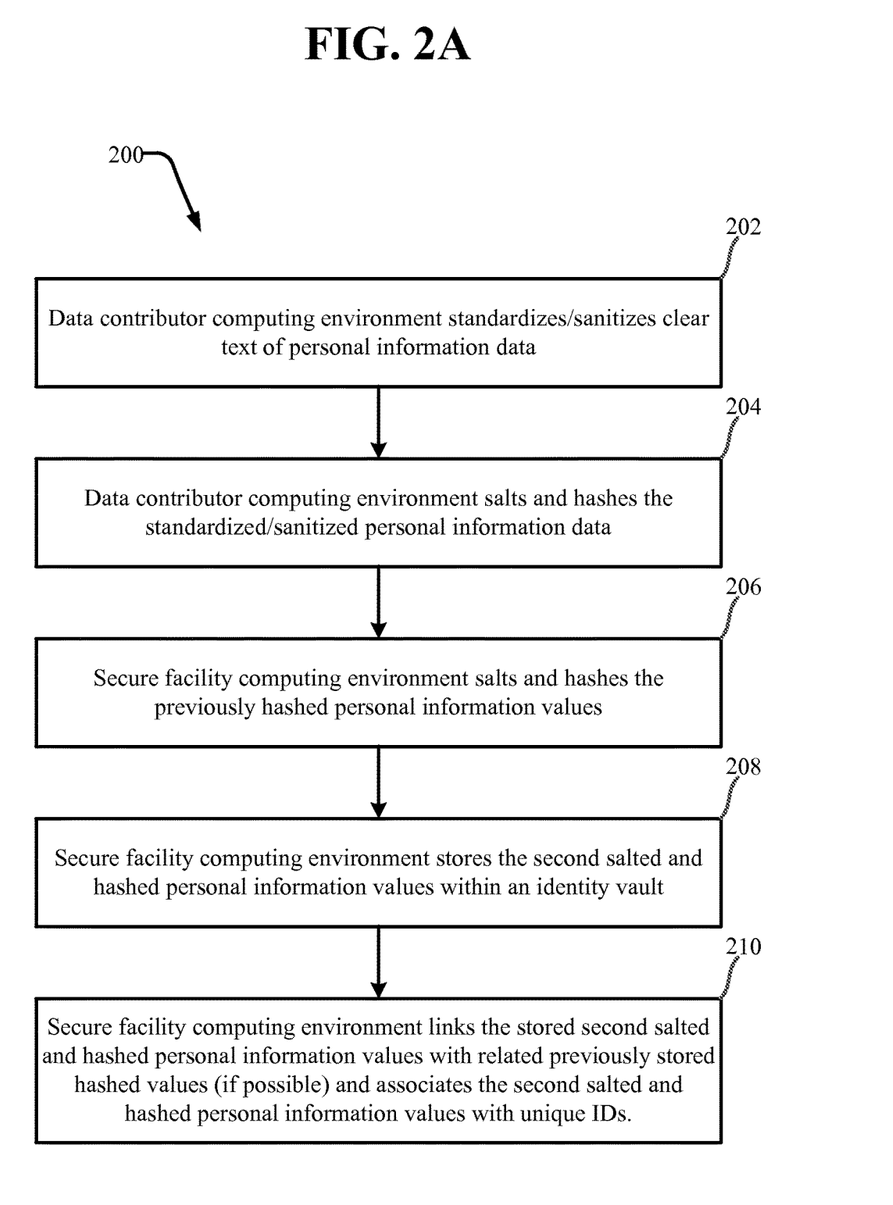
FIG. 2A is a process flow diagram illustrating a method for transforming personal information into secure personal information in the network according to the present disclosure.

Attention is now given to FIG. 2A, which illustrates a method 200 for transforming and securing personal/private/sensitive information (all referred to herein as "personal information"), according to the present disclosure. At block 202 a data contributor computing environment 102 standardizes/sanitizes clear text of personal information. At block 204 the data contributor computing environment 102 salts and hashes the standardized/sanitized personal information. At block 206 the secure facility computing environment 108 thereafter receives the cleansed information from the contributor computing environment and salts and hashes the previously cleansed/hashed personal information values. At block 208 the secure facility computing environment 108 stores the second salted and hashed personal information values within an identity vault. The identity vault contains previously stored second salted and hashed personal information values associated with unique IDs. At block 210 the secure facility computing environment 108 links the stored second salted and hashed personal information values with related previously stored hashed values (if possible as described herein below) and associates the second salted and hashed personal information values with associated unique IDs.

Figure 2B:
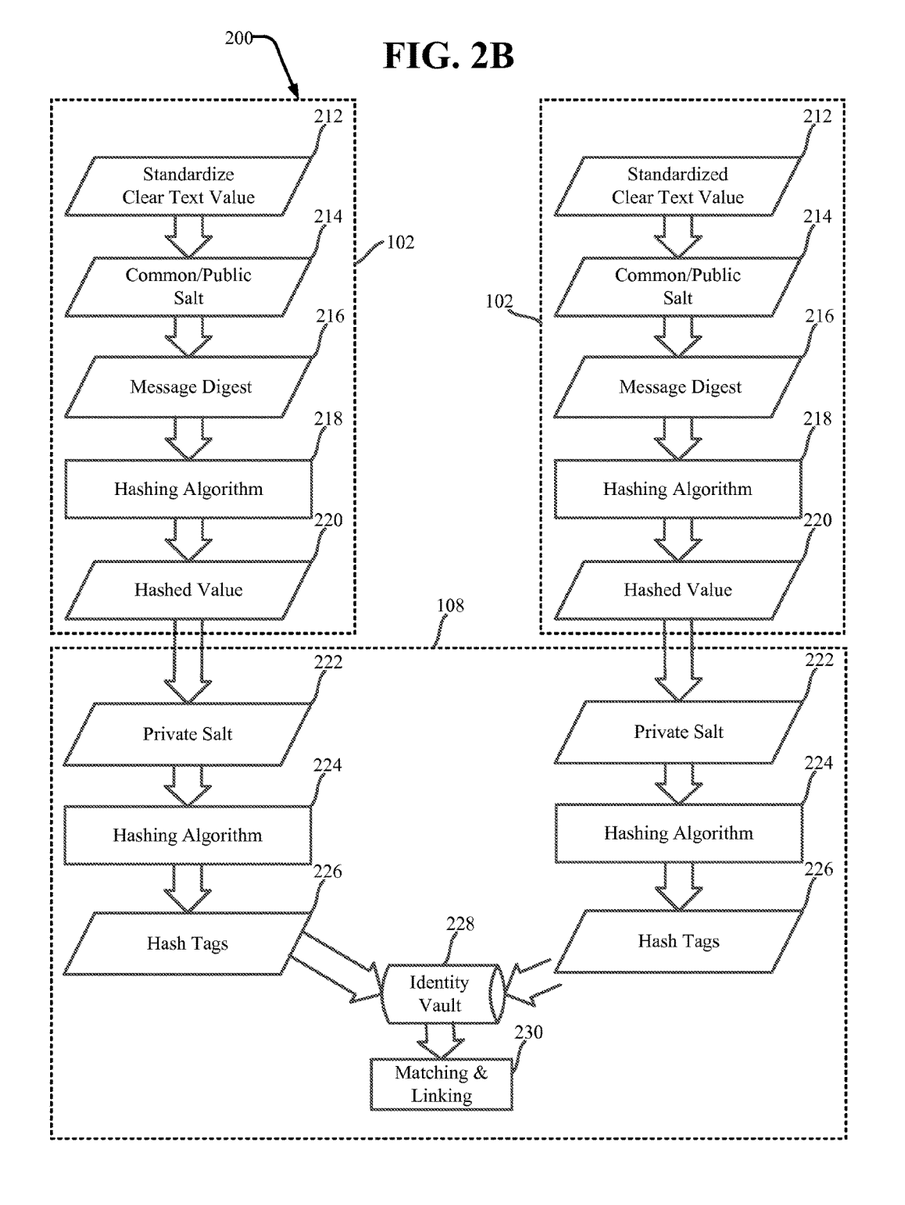
FIG. 2B is a process flow diagram further illustrating the method of FIG. 2A for transforming personal information into secure personal information by two separate and distinct data contributors in the network according to the present disclosure.

Each of the blocks illustrated in the method 200 of FIG. 2A involve multiple processing steps, which are more specifically described with reference to FIG. 2B. FIG. 2B illustrates the transformation and securing of personal information data by two separate and distinct data contributor computing environments 102. Corresponding blocks/processes of the data contributor computing environments 102 are collectively described and numbered herein because the processing of personal information data by different data contributor computing environments 102 is exactly the same. This ensures that the processing of personal information data by different data contributor computing environments 102 generates substantially similarly structured output hashed values that can be successfully linked by the secure facility computing environment 108.

Each data contributor computing environment 102 standardizes/sanitizes the personal information clear text using specific rules/logic (illustrated as 212). An illustrative and non-limiting list of personal information includes social security number (SSN), first name, last name, and address. While not being personal information, contributor IDs are also salted and hashed according to the teachings herein described. In the context of the healthcare industry, personal information may additionally include Medicare ID, Medicaid recipient number, and Medicaid family number, for example. One illustrative sanitization rule may change the clear text (which may include both upper and lower case characters) into purely upper case or purely lower case text. This rule ensures that hashing of the clear text produces identical values because, for example, "E" produces a different hashed value than "e". Another illustrative rule removes punctuation marks/characters from the clear text. Yet another illustrative rule removes spaces within the clear text. A further illustrated rule removes line ends and carriage returns from the clear text.

The standardized/sanitized text is salted using a "common salt" (illustrated as 214). The term "common salt," as used herein, refers to a single salt used by every data contributor computing environment 102. "Salting" as known to those skilled in the art is a cryptography concept that involves providing additional data, such as a common random number, as an additional input (e.g. along with confidential or private information) to a one-way function that hashes the private information.

The concatenation of the salt and sanitized clear text of the personal information becomes the message digest (illustrated as 216) that is input to and hashed using a hashing algorithm (illustrated as 218). For example, the hashing algorithm may be a one-way hashing algorithm such as SHA-256. However, one skilled in the art should appreciate that different one-way hashing algorithms may be used, depending upon the data to be hashed and the security level to be achieved. The resulting personal information hashed values (illustrated as 220) may be represented as 64 character values.

For illustration, Table 1 below depicts illustrative pre-sanitization clear text personal information and Table 2 depicts the resulting hashed values of the sanitized and salted protected personal information.

TABLE 1

Illustrative pre-sanitization clear text personal information.

| FIRST_NAME | LAST_NAME | SSN |
|---|---|---|
| Joseph | Smith | 000000000 |
| John | Smith | 111111111 |
| Jack | Smith | 222222222 |

TABLE 2

Illustrative resulting hashed values of the sanitized and salted personal information of Table 1.

| FIRST_NAME_E | LAST_NAME_E | SSN_E |
|---|---|---|
| 12343cd576727e759d144ec497e19ecem089cdmdb11578ae10a9456092mabafc1d7d | 123m812ae83f17a8488bbm9f5f0d2m74c46m94e2f42a6bd76d96614f71a6fd1efac | 123fc7cb86eff142711b4d1e2e7aead2aa6f4ce605481632a7430e0m467c79a778b |
| 1239a57m93e4f368d62e7125890ae6b5230b59024468ff85f7f8cf8443a1c8e6533 | 1231dd4m4e87f2486ee1e639a38b3e5942d68a9118b107354abacb9me34a37824cb | 123503bb674edddd4bcfda8865ad3acfb851555m44ce8325eb47be39f72f7bef345 |
| 123e0ead436f8fem1f52b91621ce9b524m53c6c5051fbbfc18cfec41744cb11m742 | 123c2edcd9b53e3b6966efb2b201f52441dd677d2987bcca3d063577e882cb6m1d9 | 123f120bb5698d520c5691b6d603am0bfd662d13bf177a04571f9d1mcm745dfa2a5 |

Once the hashed values (illustrated as 220) are communicated to and received by the secure facility computing environment 108, the hashed values are salted using a "private salt" (illustrated as 222). As used herein, the term "private salt" refers to a salt maintained within and used solely by the secure facility computing environment 108. The private salt is not communicated to the data contributor computing environments 102. This provides an additional level of security that prevents reverse engineering of hashed values into their unhashed source data.

The salted values (illustrated as 222) are hashed a second time using a one-way hashing algorithm (illustrated as 224). The second hashing of the data may produce 64 character values. As with the first hashing of the data (illustrated as 218), the SHA-256 hashing algorithm may also be used by the secure facility computing environment 108. Likewise, one skilled in the art should appreciate that different hashing algorithms may be used depending upon the type of data to be hashed and the security level to be achieved. One skilled in the art should appreciate that the hashing algorithm(s) used to hash the data (illustrated as 218 and 224) may be the same or different depending upon implementation of the present disclosure.

For illustration, Table 3 below depicts resulting second hashed values of the first hashed values of Table 2. A comparison of Tables 2 and 3 illustrates that the hashed values generated by the data contributor computing environments 102 are different from those generated by the secure facility computing environment 108. This is a direct result of the use of the different salts (i.e., public and private). This diminishes, or eliminates, the potential of the second hashed data being re-identified into its clear text source data.

TABLE 3

Illustrative resulting second hashed values of the first hashed values of Table 2.

| FIRST_NAME_E | LAST_NAME_E | SSN_E |
|---|---|---|
| 1238ca657102ae567mc8845167957a78a1cd321342ca09d82a28am53a7e5830fd89 | 123m812ae83f17a8488bbm9f5f0d2m74c46m94e2f42a6bd76d96614f71a6fd1efac | 123fcee4cf166e0f1d0c110338942f6a8cb1049e78c594ef49952aed348cdde3e63 |
| 123bff7m485135c547322b677792b39m0d8b08bc8896m9m3699a3bmb6e7b6e205a | 1231dd4m4e87f2486ee1e639a38b3e5942d68a9118b107354abacb9me34a37824cb | 1237546m08f4857e29c90f3ffc3e7509ee072b9234b38a2f3a1a9d53em0641d6456 |
| 1232e6c27e28c72a14a20c07e138d45d7fca52333f673f560fc4678c734db8ddaf1 | 123c2edcd9b53e3b6966efb2b201f52441dd677d2987bcca3d063577e882cb6m1d9 | 123b5e9329e72f942c27ea570a1946de34b10463f55ef366c89556a2a5bf372e634 |

The different fields run through the hashing algorithm may be tagged with a hash tag 226 effectively identifying the field of the hashed value prior to storage in an identity vault, or the hashed value output of the hashing algorithm 224 may be the hash tag 226 for direct storage in the identity vault. The second hashed values, in either event, are thereafter stored within the identity vault (such as the identity vault 120) (illustrated as 228).

Once stored in the identity vault, the second hashed values are matched and linked to previously stored second hashed values, when possible (illustrated as 230). Matching and linking of the data involves the use of unique IDs. Each unique ID is associated with data representative of a specific individual. The recently stored second hashed data either receives a newly generated unique ID (when the individual associated with the recently stored data is not represented by previously stored data within the identity vault) or it receives a unique ID previously generated (when the individual associated with the recently stored data is represented by previously stored data stored within the identity vault).

Figure 3:
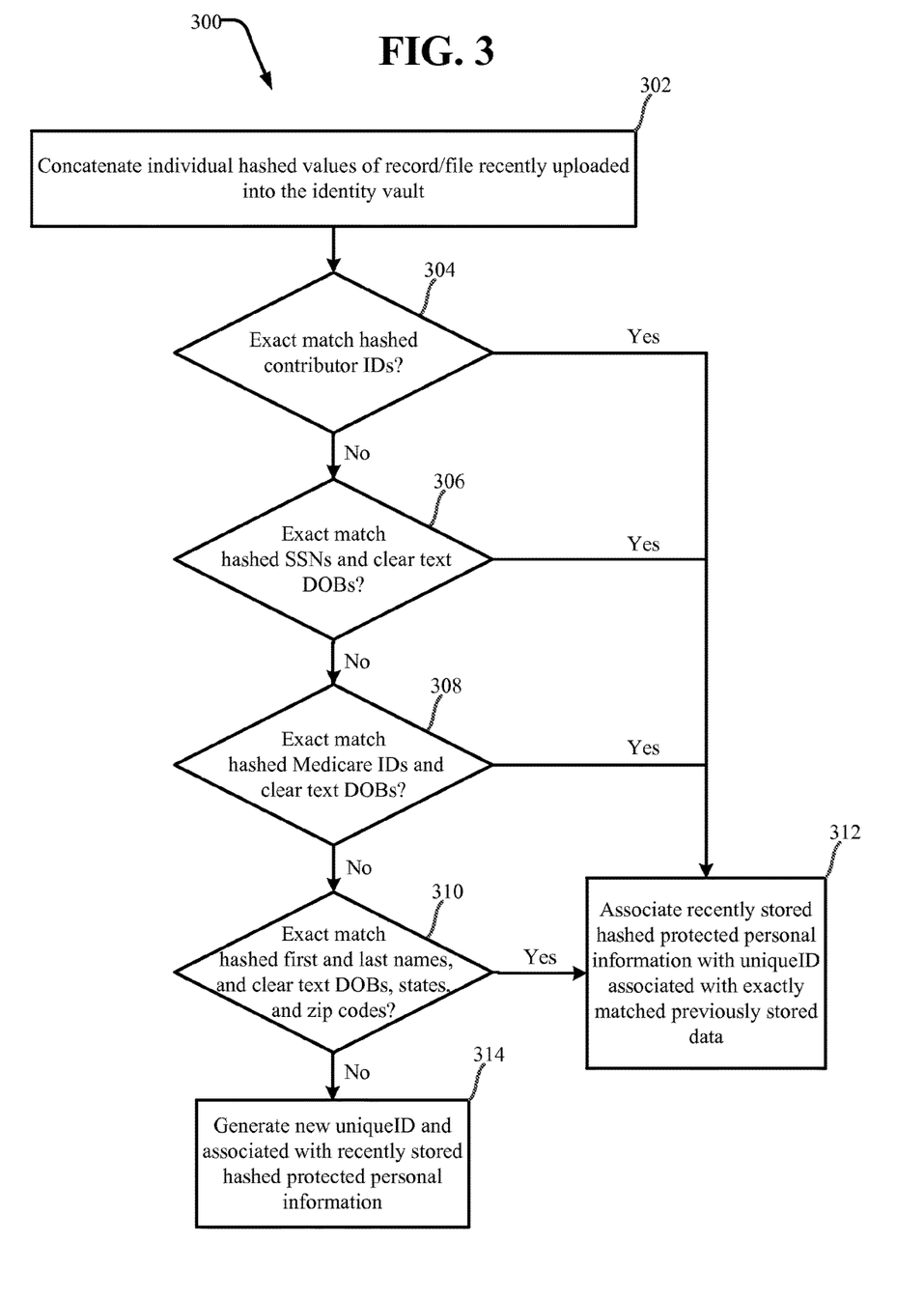
FIG. 3 is a process flow diagram illustrating a method for matching and linking hashed data values of an identity vault using unique IDs according to the present disclosure.

A method 300 for generating a unique ID and matching and linking hashed data values to the identity vault is described with reference to FIG. 3. The individual hashed values (e.g., contributor ID, SSN, first name, last name, address, DOB, etc.) are concatenated for each record/file uploaded into the identity vault (illustrated as 302). In an illustrative healthcare industry example, the individual hashed values may additionally include a Medicare ID. A processor determines whether an exact match exists between the recently uploaded/stored hashed contributor ID value and a previously stored hashed contributor ID value (illustrated as 304). The processor may also determine whether an exact match exists between the recently stored hashed SSN value and associated clear text DOB value, and previously stored hashed SSN values and their associated clear text DOB values (illustrated as 306). The processor may further determine whether an exact match exists between the recently stored hashed Medicare ID value and its associated clear text DOB value, and previously stored hashed Medicare ID values and their associated clear text DOB values (illustrated as 308). The processor may additionally determine whether an exact match exists between the recently stored hashed first name value, hashed last name value, and their associated clear text DOB value, state value, and zip code value, and previously stored hashed first name values, hashed last name values, and their associated clear text DOB values, state values, and zip code values (illustrated as 310). If any matches are determined to exist, the unique ID associated with the matching previously stored data is associated with the recently stored data (illustrated as 312). Linking of the data ensures that stored hashed personal information of an individual is associated within the identity vault. This provides a robust data set for research purposes. Alternatively, if no matches are determined to exist, a new, non-previously generated unique ID is generated and associated with the recently stored hashed personal information (illustrated as 314). If the recently stored hashed data is the first batch of data received from a specific data contributor computing environment 102, decision point 304 may be omitted because no matching hashed contributor ID for that contributor will exist in the identity vault.

If an exact match is determined between the recently stored hashed data value and previously stored data, the processor may compare all demographic values of the recently stored data (including both hashed and clear text values) to analogous values of the matching previously stored data (not illustrated). Each generated unique ID may be an alpha, numeric, or alphanumeric value.

Figure 4A:
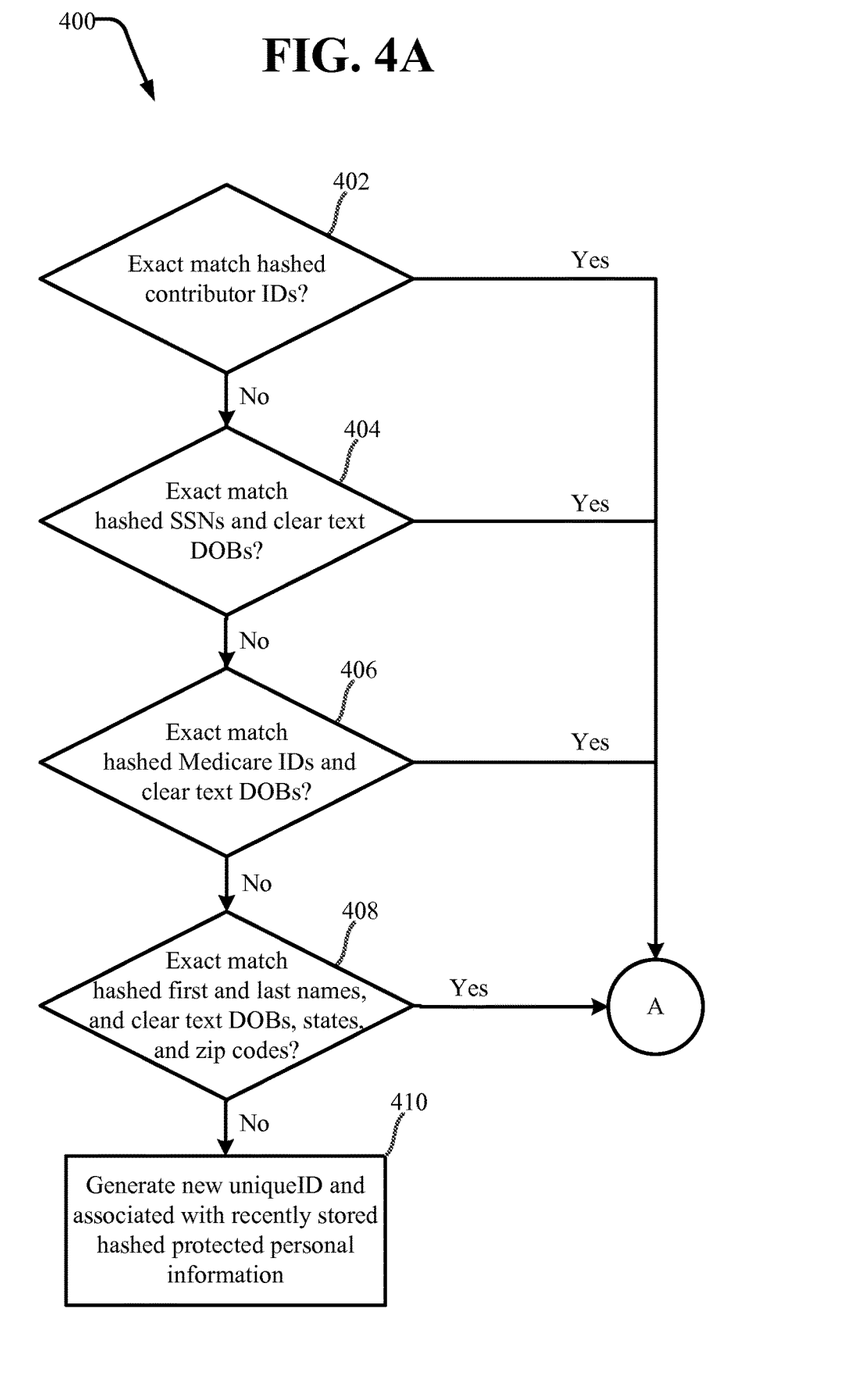
FIGS. 4A and 4B are process flow diagrams illustrating a method for rekeying/restating previously generated unique IDs according to the present disclosure.
Figure 4B:
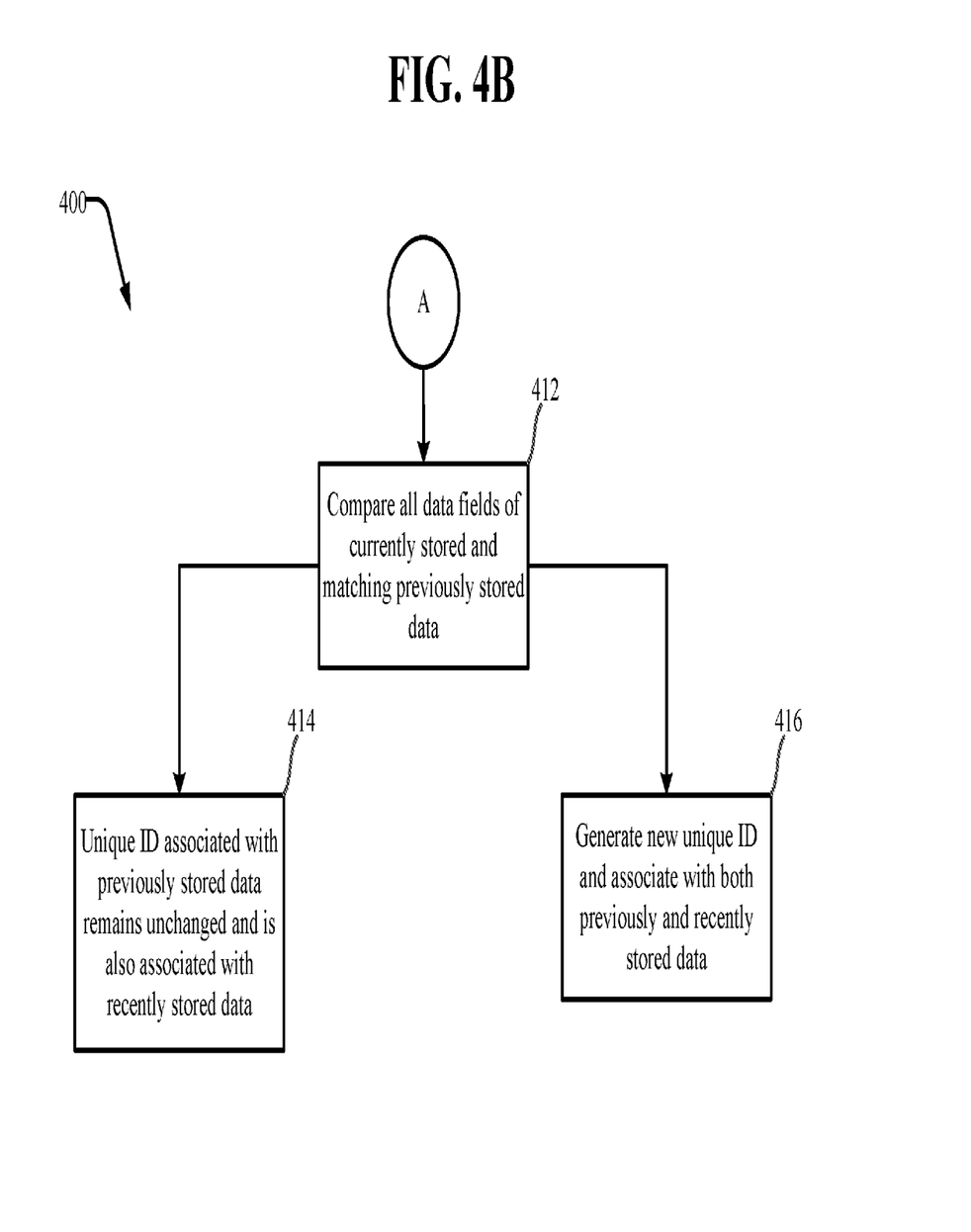

Referring now to FIGS. 4A and 4B, a method 400 for rekeying/restating previously generated unique IDs is described. A unique ID associated with specific hashed data may need to be restated/altered when additional data is subsequently stored within the identity vault. Restating of unique IDs may involve a rekey process. For example, when subsequently stored hashed data includes an additional data element/field value not present in the previously stored data, the unique ID of the previously stored data may be altered/ rekeyed and applied to both the previously and subsequently stored and related hashed data. According to an example, stored hashed data may be a bridge record that associates multiple hashed data files. If the bridge record gets deleted/ corrupted (e.g., during maintenance of the secure facility computing environment 108), the unique ID associated with the bridge record may need to be restated for the bridge record and/or any associated records/data files.

Rekeying may involve determining whether an exact match exists between a recently uploaded/stored hashed contributor ID value and previously stored hashed contributor ID values (illustrated as 402). Rekeying may also include determining whether an exact match exists between a recently stored hashed SSN value and its associated clear text DOB value, and previously stored hashed SSN values and their associated clear text DOB values (illustrated as 404). Rekeying may further involve determining whether an exact match exists between a recently stored hashed Medicare ID value and its associated clear text DOB value, and previously stored hashed Medicare ID values and their associated clear text DOB values (illustrated as 406). Additionally, rekeying may include determining whether an exact match exists between recently stored hashed first and last name values, and their associated clear text DOB value, state value, and zip code value, and previously stored hashed first and last name values, and their associated clear text DOB values, state values, and zip code values (illustrated as 408). While the described rekeying processes are identical to those used for matching/linking data described herein with respect to FIG. 3, one skilled in the art should appreciate that the logics/processes used in the rekeying and matching/linking processes may be different.

If it is determined that no matches exist, a new unique ID is generated for and associated with the recently stored hashed data (illustrated as 410). Conversely, if it is determined that a match exists, all data fields of the currently stored and matching previously stored data are compared (illustrated as 412). If there is an exact match across all of the data fields, the unique ID associated with the previously stored data remains unchanged, and is also associated with the recently stored data (illustrated as 414). Alternatively, if the hashed contributor ID values match and at least one demographic data field (e.g., DOB, state, zip code, etc.) of the recently stored data is not present in the previously stored data, a new unique ID is generated and associated with both the previously and recently stored data (illustrated as 416). When step 416 occurs, the previously stored data is no longer associated with its previous unique ID.

Figure 5:
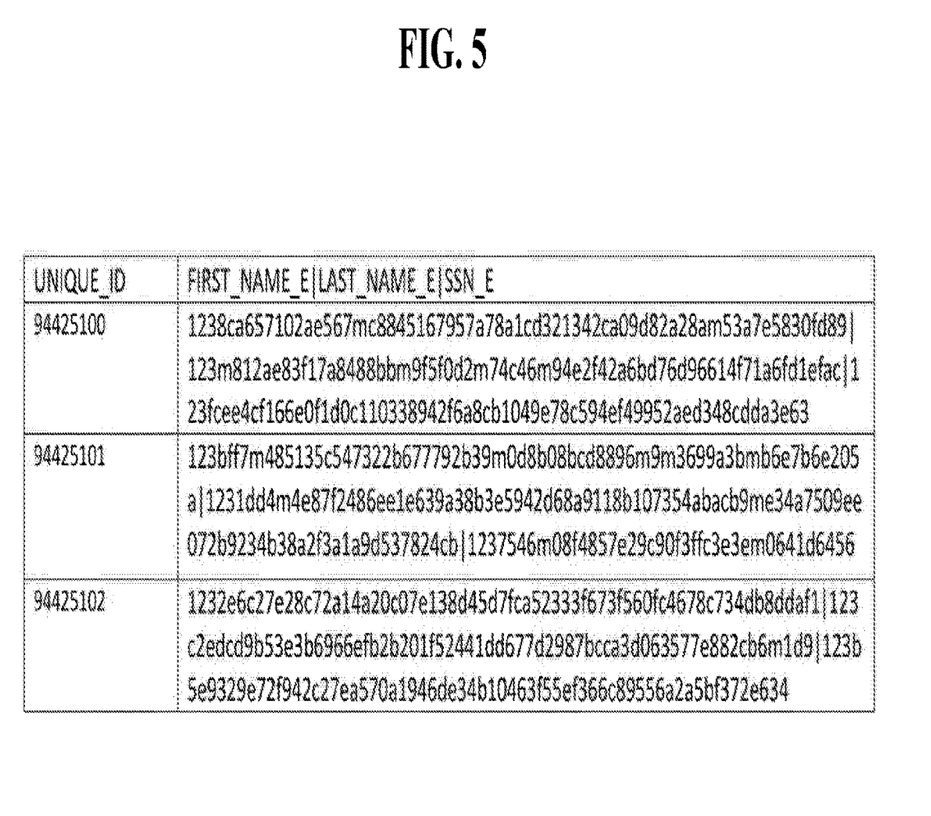
FIG. 5 illustrates an example data structure representation of unique IDs and associated concatenated hashed values within the identity vault according to the present disclosure.
Figure 6:
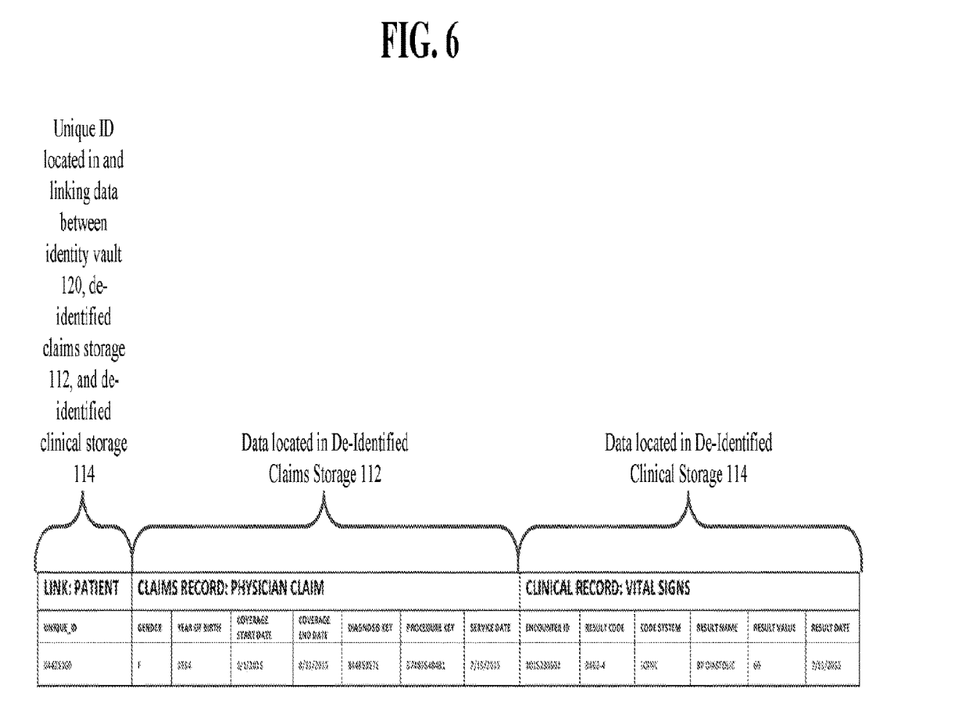
FIG. 6 illustrates an example of how related claims data and clinical record data may be associated across various data storages using a unique ID in a healthcare data embodiment of a network according to the present disclosure.

FIG. 5 illustrates how unique IDs and their associated concatenated hashed values may be represented within the identity vault. As stated above with respect to FIG. 1, once a unique ID is associated with the recently loaded hashed personal information, the same unique ID is also associated with the clear text data (e.g., within the de-identified claims and clinical storages 116, 118) to which it relates. FIG. 6 illustrates how related healthcare claims data and clinical record data may be associated across data storages via a unique ID. The data format illustrated in FIG. 6 may be how data is represented within a data dictionary.

Figure 7:
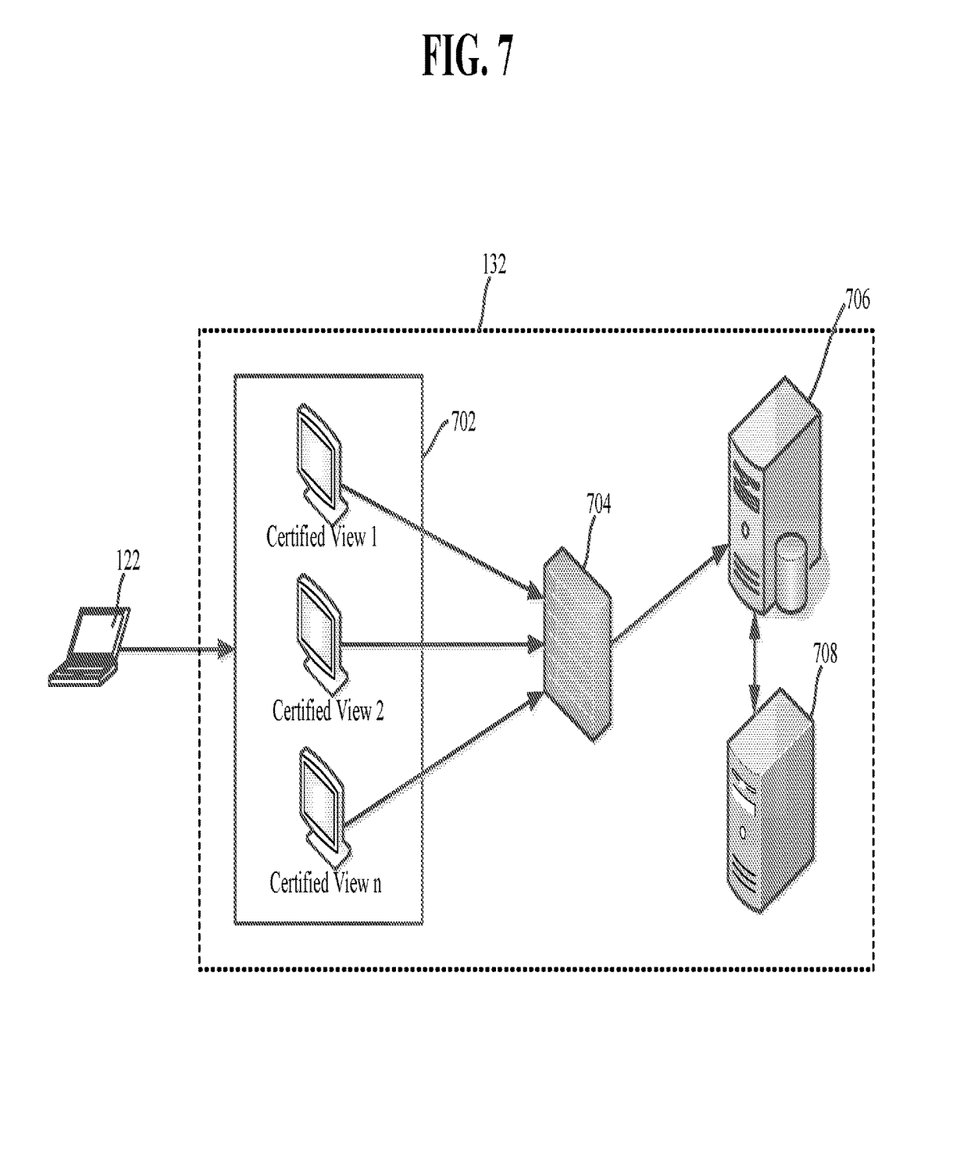
FIG. 7 illustrates a system architecture of the virtual private network (VPN) illustrated in FIG. 1 according to the present disclosure.

Attention is now given to FIG. 7, which illustrates the system architecture of the VPN 132 illustrated in FIG. 1. A researcher, via a computing device 122, accesses certified views for which the researcher has been granted access. Each researcher may be granted access to a single certified view or multiple certified views. When a researcher properly authenticates a session (as described in detail below) the VPN 132 accesses certified views of the researcher from the certified view storage 130 of the data access zone 128 (illustrated in FIG. 1) and places them in a sandbox 702. The sandbox 702 provides a researcher with access to all of its authorized views during a single session. Each certified view may correspond with one virtual desktop interface (VDI). For example, a researcher that has access to two (2) certified views may be presented with two (2) VDIs upon accessing the virtual private network (VPN) 132. This separation of the certified views eliminates the possibility of a researcher with access to multiple certified view combining data from two or more certified views, thereby effectively limiting the risk of personal information re-identification.

Access by the researcher computer 122 to the certified view via the VPN 132 may be restricted by a two factor authentication. An illustrative two factor authentication includes (1) a username and password factor and (2) a phone factor. Each of the authentication factors may use secure protocols and may be stored in an encrypted manner. The username and password factor may involve the researcher inputting a username and password specific to a particular directory on their computing device 122. Once the username and password credentials are supplied, the researcher is prompted to perform the second (i.e., phone factor) authentication. This authentication may be performed a variety a ways. For example, the VPN 132 may cause the researcher's phone to receive a call. To authenticate, the researcher answers the phone call and provides a personal identification number (PIN). In another example, the VPN 132 causes the researcher's phone to receive a text message. To authenticate, the researcher responds to the text message using the PIN. In another example, the VPN 132 may cause an app on the researcher's phone to receive a notification. To authenticate, the researcher accesses the app, inputs the PIN, and selects "authenticate."

The two factor authentication information (i.e., username, password, and PIN) are communicated from the researcher computer 122 through a firewall 704 to an analytics server 706. For example, the analytics server 706 may be the NETEZZA MAKO® server produced by International Business Machines Corporation (IBM). To authenticate the researcher within the VPN 132, the analytics server 706 communicates with an authentication server 708. The authentication server may be a lightweight directory access protocol (LDAP) server.

Although aspects of the present disclosure are described with respect to examples in a health care data environment, it should be understood that various disclosed techniques can be used in numerous other fields of technology in which sensitive information needs to be transformed, secured, and provided to individuals on a limited and controlled access basis. Various applications of the disclosed techniques provide substantial improvements to the functioning of the computer apparatus and the technical environments in which the various applications are implemented.

Moreover, although the present disclosure has been described herein with reference to the accompanying drawings, it is to be understood that the present disclosure is not limited to those precise teachings, and that various other changes and modifications may be made by one skilled in the art without departing from the spirit and scope of the present disclosure.

What is claimed is:

1. A highly secure system for transforming and securing personal information, comprising:
a data contributor computing environment including a hardware processor configured to:
sanitize clear text personal information; and
transform, using a common salt and a first hashing algorithm, the sanitized clear text personal information into first hashed values; and
a secure facility computing environment including a hardware processor configured to:
receive the first hashed values and corresponding clear text non-personal information from the data contributor computing environment;
store the clear text non-personal information within a plurality of data storages;
transform, using a private salt and a second hashing algorithm, the first hashed values into second hashed values, the private salt being inaccessible by the data contributor computing environment;
store the second hashed values within an identity vault, the identity vault including previously stored hashed values associated with unique IDs, each unique ID corresponding to a single individual;
link the second hashed values to previously stored hashed values;
associate in a first storage each of the second hashed values with a unique ID;
associate in a second storage each stored clear text non-personal information with a unique ID associated with a corresponding second hashed value;
analyze a data dictionary for compliance with an admin schema storage of a data storage zone, the admin schema storage relating to rules for clarity standards for the data dictionary, the data dictionary including data from the plurality of data storages;
communicate, when the data dictionary is compliant with the clarity standards, the data dictionary to a data access zone with a certified view storage, the certified view storage storing the data dictionary;
generate one or more independent certified views approved for viewing by a researcher, each of the one or more certified views based on the analysis of the data dictionary and stored in the certified view storage; and
securely control, using a virtual private network, access to the one or more independent certified views by a researcher computer with one or more corresponding virtual desktop interfaces, the virtual private network is configured to prevent the research computer from communicating data from one virtual desktop interface to another virtual desktop interface.

2. The system of claim 1, wherein the clear text personal information is sanitized by at least one of changing the clear text into purely upper case or purely lower case text, removing punctuation marks from the clear text, removing spaces from the clear text, or removing line ends from the clear text.

3. The system of claim 1, wherein the second hashed values are linked to previously stored hashed values by determining the satisfaction of at least one of the following:
(i) an exact match between hashed contributor ID values;
(ii) an exact match between hashed social security number values and clear text date of birth values;
(iii) an exact match between hashed Medicare ID values and clear text date of birth values; and
(iv) an exact match between hashed first name values, hashed last name values, clear text date of birth values, clear text state address values, and clear text zip code values.

4. The system of claim 1, wherein the virtual private network is configured to present access to multiple certified views to a single researcher computing device.

5. The system of claim 1, wherein:
the first hashing algorithm and the second hashing algorithm are the same one-way hashing algorithm; and the virtual private network requires a researcher perform a two factor authentication process in order to gain access to the certified view.

6. A method for transforming, securing, and transmitting personal information in a computer network that includes contributor computing devices and researcher computing devices, the method comprising the steps of:
receiving sanitized, first hashed personal information values and corresponding clear text data from the data contributor computing devices;
transforming the sanitized, first hashed personal information values into second hashed personal information values;
linking the second hashed personal information values to data values previously stored in an identity vault, linking of at least some of the second hashed personal information values to at least some of the data values previously stored in an identity vault including use of unique IDs;
generating a data dictionary in response to receiving research project parameters, the data dictionary including clear text data from multiple data storages, at least some of the clear text data being associated by unique IDs;
analyzing the data dictionary for compliance with an admin schema storage of a data storage zone, the admin schema storage having compliance rules relating to data clarity standards for the data dictionary;
communicating, when the data dictionary is determined compliant with the compliance rules, the data dictionary to a data access zone with a certified view storage, the certified view storage storing the data dictionary;
storing the data dictionary as one or more independent certified views approved for viewing by a researcher, each of the one or more independent certified views based on the analysis of the data dictionary and stored in the certified view storage, when the data dictionary clear text data is determined compliant with the compliance rules; and
providing restricted access to the one or more independent certified views, data dictionary, clear text data, and associated unique IDs to at least one of the researcher computing devices via separate and secure virtual desktop interfaces using a virtual private network configured to prevent data communication from one virtual desktop interface to another virtual desktop interface.

7. The method of claim 6, wherein the sanitized, first hashed personal information values are generated using text manipulation processes, a common salt, and a one-way hashing algorithm.

8. The method of claim 7, wherein the text manipulation processes, the common salt, and the one-way hashing algorithm are identically used by the various data contributor computing devices.

9. The method of claim 6, wherein each of the virtual desktop interfaces provides access to one certified view.

10. The method of claim 6, further comprising the step of:
updating the unique ID associated with particular second hashed personal information values when subsequently linked second hashed personal information values associated with the particular second hashed personal information values includes at least one data field not present in the particular second hashed personal information values.

11. The method of claim 6, wherein:
the sanitized, first hashed personal information values are generated using a common salt used by all of the data contributor computing devices; and
the second hashed personal information values are generated using a private salt inaccessible to the data contributor computing devices and researcher computing devices.

12. A secure computing environment for transforming, securing, and transmitting personal information, comprising:
a processor; and
a memory device including instructions operable to be executed by the processor to perform a set of actions, and configuring the processor to:
receive sanitized, first hashed personal information values and corresponding clear text data via a network exchange;
transform the sanitized, first hashed personal information values into second hashed personal information values;
link, using unique IDs, the second hashed personal information values to previously stored hashed data values;
generate a data dictionary in response to receiving research project parameters, the data dictionary including clear text data from multiple data storages, at least some of the clear text data being associated by unique IDs;
analyze the data dictionary for compliance with an admin schema storage of a data storage zone, the admin schema storage having compliance rules relating to data clarity standards for the data dictionary;
communicating, when the data dictionary is determined compliant with the compliance rules, the data dictionary to a data access zone with a certified view storage, the certified view storage storing the data dictionary;
store the data dictionary as one or more independent certified views approved for viewing by a researcher, each of the one or more independent certified views based on the analysis of the data dictionary and stored in the certified view storage, when the data dictionary clear text data is determined compliant with the compliance rules; and
provide restricted access to the one or more independent certified views, data dictionary and clear text data via separate and secure virtual desktop interfaces using a virtual private network, the virtual private network is configured to prevent data communication from one virtual desktop interface to another virtual desktop interface.

13. The secure computing environment of claim 12, wherein the sanitized, first hashed personal information values and corresponding clear text data are received from healthcare provider computing devices.

14. The secure computing environment of claim 13, wherein the sanitized, first hashed personal information values are hashed by the healthcare provider computing devices using a single common salt.

15. The secure computing environment of claim 12, wherein providing restricted access to the clear text data includes compiling certified views approved for a single researcher into a single storage.

16. The secure computing environment of claim 12, wherein the second hashed personal information values are generated using a private salt inaccessible to third party devices.

17. The secure computing environment of claim 12, wherein the processor is further configured to generate a new unique ID for second hashed personal information values when the second hashed personal information values do not link with previously stored hashed data values.

18. The secure computing environment of claim 12, wherein the sanitized, first hashed personal information values are represented as 64 character values.

19. The secure computing environment of claim 12, wherein the second hashed personal information values associated with a single individual record are concatenated prior to being linked using unique IDs.

\* \* \* \* \*